United States Patent
Nishikaze (10) Patent No.: US 11,187,630 B2
(45) Date of Patent: Nov. 30, 2021

(54) METHOD FOR PREPARING ANALYTICAL SAMPLE, ANALYSIS METHOD, AND KIT FOR PREPARING ANALYTICAL SAMPLE

(71) Applicant: SHIMADZU CORPORATION, Kyoto (JP)

(72) Inventor: Takashi Nishikaze, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 150 days.

(21) Appl. No.: 16/547,691

(22) Filed: Aug. 22, 2019

(65) Prior Publication Data

US 2020/0064234 A1 Feb. 27, 2020

(30) Foreign Application Priority Data

Aug. 24, 2018 (JP) .............................. JP2018-157701

(51) Int. Cl.
*G01N 1/28* (2006.01)
*G01N 30/06* (2006.01)
*H01J 49/00* (2006.01)

(52) U.S. Cl.
CPC .............. *G01N 1/28* (2013.01); *G01N 30/06* (2013.01); *G01N 2560/00* (2013.01); *H01J 49/0031* (2013.01)

(58) Field of Classification Search
None
See application file for complete search history.

(56) References Cited

U.S. PATENT DOCUMENTS

2018/0059094 A1 3/2018 Nishikaze

FOREIGN PATENT DOCUMENTS

| EP | 3 279 655 A1 | 2/2018 |
| EP | 3 343 225 A1 | 7/2018 |
| JP | 2013-068594 A | 4/2013 |
| JP | 6135710 B2 | 5/2017 |

OTHER PUBLICATIONS

Nishikaze, T. et al. Differentiation of Sialyl Linkage Isomers by One-Pot Sialic Acid Derivatization for Mass Spectrometry-Based Glycan Profiling, Anal. Chem. 2017, 89, 2353-2360 (Year: 2017).*
Communication dated Mar. 2, 2020 from European Patent Office in EP Application No. 19192493.5.
Takashi Nishikaze et al., "Differentiation of Sialyl Linkage Isomers by One-Pot Sialic Acid Derivatization for Mass Spectrometry-Based Glycan Profiling", Analytical Chemistry, 2017, pp. 2353-2360, vol. 89, Issue 4.

* cited by examiner

*Primary Examiner* — Xiaoyun R Xu
(74) *Attorney, Agent, or Firm* — Sughrue Mion, PLLC (57) ABSTRACT

A method for preparing an analytical sample for analyzing a glycan contained in a sample includes: performing a first reaction so that when sialic acid is linked to the glycan, sialic acid of a first linkage type is lactonized and modification different from lactonization is performed on sialic acid of a second linkage type different from the first linkage type; performing a second reaction to ring-open a lactone formed in the first reaction; and performing the first reaction again.

15 Claims, 2 Drawing Sheets

METHOD FOR PREPARING ANALYTICAL SAMPLE, ANALYSIS METHOD, AND KIT FOR PREPARING ANALYTICAL SAMPLE

INCORPORATION BY REFERENCE

The disclosure of the following priority application is herein incorporated by reference: Japanese Patent Application No. 2018-157701 filed Aug. 24, 2018

TECHNICAL FIELD

The present invention relates to a method for preparing an analytical sample, an analysis method, and a kit for preparing an analytical sample.

BACKGROUND ART

Sialic acid is a saccharide abundantly present in a biological body. Sialic acid is included in glycans linked to protein in the biological body, and is often present at a non-reducing end of a glycan. Thus, sialic acid is positioned on the outermost side of such a glycoprotein molecule and plays an important role because it is directly recognized by other molecules.

Sialic acid may have different linkage types to the adjacent saccharide. For example, $\alpha 2,3$- and $\alpha 2,6$-linkage types are primarily known for human N-linked glycans (N-glycans), and in addition to these linkage types, $\alpha 2,8$- and $\alpha 2,9$-linkage types are known for O-linked glycans (O-glycans) and glycosphingolipids. Sialic acids with such different linkage types are recognized by different molecules, and thus can play different roles. In addition, sialic acid in expressed glycoprotein is known to undergo change in linkage type in association with oncogenesis, and expected to be usable as a biomarker for cancers. Moreover, glycosylation is known to affect the effect of biopharmaceutical products, and hence analysis of the linkage type of sialic acid is also important in quality control of biopharmaceutical products.

However, analysis of a sialylated glycan containing sialic acid by mass spectrometry is not easy because sialic acid is less likely to be ionized in positive ion mode due to its negative charge and is easily decomposed. PTL 1 discloses that sialic acid in a glycan is stabilized by amidation in a non-aqueous solvent. However, the method disclosed in PTL 1 cannot differently modify sialic acid depending on its linkage type. Further, the mass of a glycan does not originally change depending on the linkage type of sialic acid, and therefore, in the case of the method disclosed in PTL 1, sialic acids of different linkage types cannot be differentiated when analyzed by mass spectrometry.

Chemical derivatization methods to modify sialic acid in a linkage-specific manner have been proposed for type-by-type analysis of the linkage type of sialic acid. In such chemical derivatization methods, which utilize the higher tendency of $\alpha 2,3$-sialic acid to undergo intramolecular dehydration by a dehydration condensation agent than that of $\alpha 2,6$-sialic acid, $\alpha 2,3$-sialic acid is lactonized through intramolecular dehydration and $\alpha 2,6$-sialic acid is simultaneously reacted with a nucleophilic agent such as an alcohol or an amine. Molecules then formed have different masses depending on the linkage type of the sialic acid, and hence the linkage type of sialic acid can be analyzed in a type-specific manner through mass spectrometry. PTL 2 and NPTL 1 disclose a method in which $\alpha 2,3$-sialic acid is lactonized and $\alpha 2,6$-sialic acid is amidated by adding a solution including isopropylamine and a dehydration condensation agent to a free glycan.

CITATION LIST

Patent Literature

PTL1: JP 2013-68594 A
PTL2: JP 6135710 B

Non-Patent Literature

NPTL1: Nishikaze T, Tsumoto H, Sekiya S, Iwamoto S, Miura Y, Tanaka K. "Differentiation of Sialyl Linkage Isomers by One-Pot Sialic Acid Derivatization for Mass Spectrometry-Based Glycan Profiling" Analytical Chemistry, (USA), ACS Publications, Feb. 21, 2017, Volume 89, Issue 4, pp. 2353-2360

SUMMARY OF INVENTION

Technical Problem

The present inventor has found that when the method disclosed in PTL 2 and NPTL 1 is performed, there is a case where reaction specificity is reduced particularly in O-linked glycans so that part of $\alpha 2,6$-sialic acids are lactonized.

Solution to Problem

According to the 1st aspect of the present invention, a method for preparing an analytical sample for analyzing a glycan contained in a sample comprises: performing a first reaction so that when sialic acid is linked to the glycan, sialic acid of a first linkage type is lactonized and modification different from lactonization is performed on sialic acid of a second linkage type different from the first linkage type; performing a second reaction to ring-open a lactone formed in the first reaction; and performing the first reaction again.

According to the 2nd aspect of the present invention, in the method for preparing an analytical sample according to the 1st aspect, it is preferred that the lactone formed by lactonization of the sialic acid of the second linkage type is ring-opened in the second reaction.

According to the 3rd aspect of the present invention, it is preferred that the method for preparing an analytical sample according to the 1st or 2nd aspect further comprises repeatedly performing an operation to perform the second reaction and an operation to perform the first reaction alternately a predetermined number of times equal to or more than 1.

According to the 4th aspect of the present invention, in the method for preparing an analytical sample according to any one of the 1st to 3rd aspects, it is preferred that the second reaction is performed by bringing the sample subjected to the first reaction into contact with a basic solvent having a pH of 8 or higher.

According to the 5th aspect of the present invention, in the method for preparing an analytical sample according to any one of the 1st to 4th aspects, at least one of reactions including the first reaction and the second reaction is performed in a state where the glycan is bound or adsorbed to a solid phase carrier.

According to the 6th aspect of the present invention, in the method for preparing an analytical sample according to any one of the 1st to 5th aspects, the sample contains an O-linked glycan.

According to the 7th aspect of the present invention, in the method for preparing an analytical sample according to any one of the 1st to 6th aspects, the modification is esterification or amidation.

According to the 8th aspect of the present invention, in the method for preparing an analytical sample according to any one of the 1st to 7th aspects, the lactone formed by the first reaction is subjected to modification different from the modification performed on sialic acid of the second linkage type.

According to the 9th aspect of the present invention, in the method for preparing an analytical sample according to any one of the 1st to 8th aspects, the sialic acid of the first linkage type is at least one of α2,3-sialic acid, α2,8-sialic acid, and α2,9-sialic acid, and the sialic acid of the second linkage type is α2,6-sialic acid.

According to the 10th aspect of the present invention, an analysis method comprises: preparing an analytical sample by the method for preparing an analytical sample according to any one of 1st to 9th aspects; and analyzing the prepared analytical sample.

According to the 11th aspect of the present invention, in the analysis method according to the 10th aspect, it is preferred that the prepared analytical sample is analyzed by at least one of mass spectrometry and chromatography.

According to the 12th aspect of the present invention, a kit for preparing an analytical sample for use in the method for preparing an analytical sample according to the 4th aspect comprises: a basic solvent having a pH of 8 or higher.

Advantageous Effects of Invention

According to the present invention, it is possible to more accurately modify sialic acid in a linkage-specific manner.

DESCRIPTION OF EMBODIMENTS

Hereinbelow, embodiments of the present invention will be described with reference to the drawings.

Figure 1:
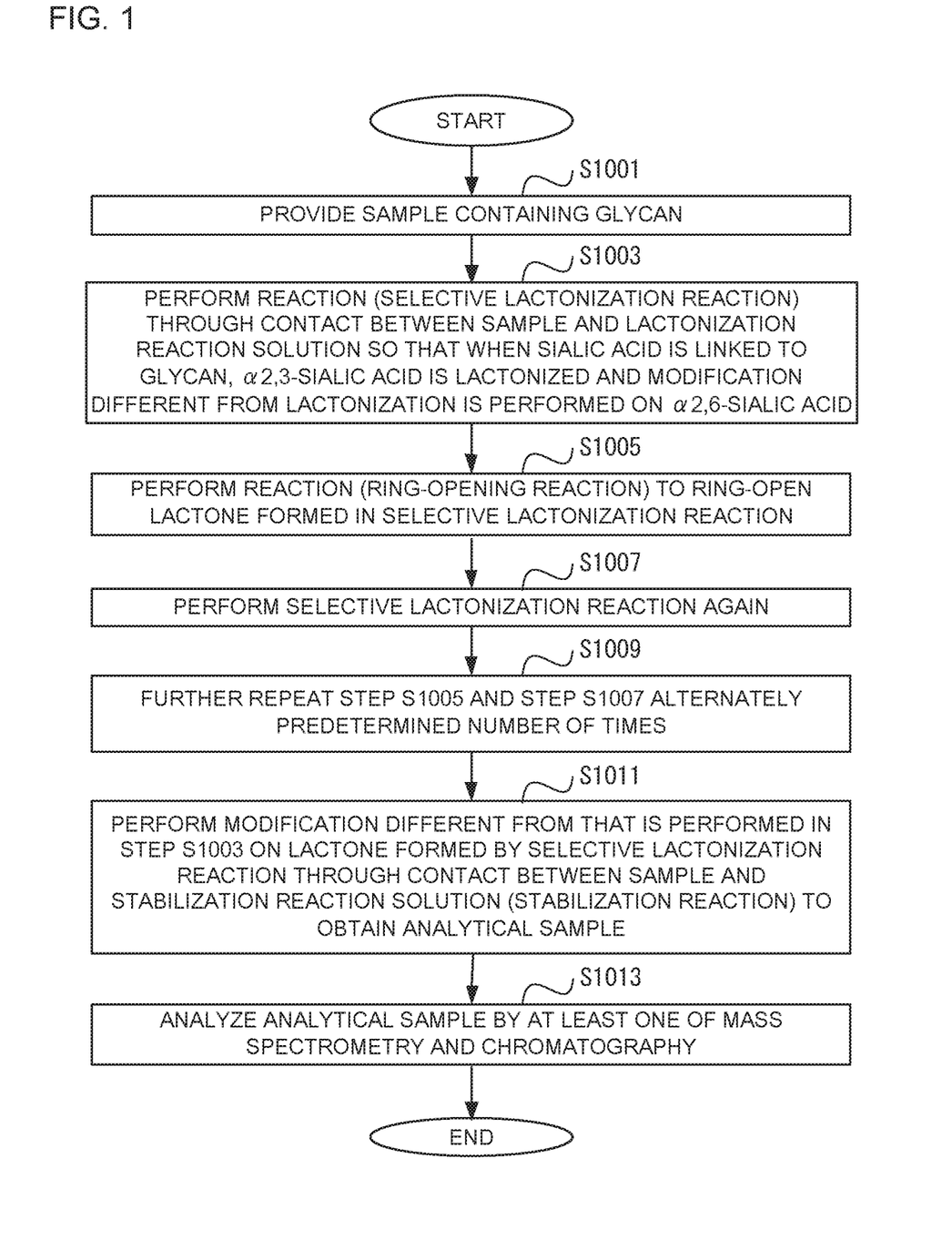
FIG. 1 is a flowchart illustrating the procedure of an analysis method according to one embodiment.

FIG. 1 is a flowchart illustrating the procedure of an analysis method related to a method for preparing an analytical sample (sample for analysis) of the present embodiment. In a step S1001, a sample containing a glycan is provided.

The sample containing a glycan is not particularly limited, and may contain at least one molecule selected from the group consisting of a free glycan, a glycopeptide and a glycoprotein, and a glycolipid. The method for preparing an analytical sample according to the present embodiment is suitable for use in the analysis of the linkage type of sialic acid in a glycan. Therefore, the sample preferably contains a glycan that may have sialic acid at its end, such as an N-linked glycan, an O-linked glycan, or a glycolipid-type glycan. The present inventor has found that when α2,6-sialic acid is to be selectively amidated by the conventional linkage-specific sialic acid derivatization method, there is a case where α2,6-sialic acid is lactonized in an O-linked glycan, and arrived at the present invention. Therefore, the sample preferably contains an O-linked glycan having α2,6-sialic acid. However, even when the sample contains another glycan, the same effect can be obtained by the present invention when there is a possibility that unintended lactonization may occur in the linkage-specific modification of sialic acid.

When the sample contains a free glycan, a glycan released from a glycoprotein, a glycopeptide, or a glycolipid may be used. Examples of a method that can be used to release a glycan from a glycoprotein, a glycopeptide, or a glycolipid include enzymatic treatment using O-glycosidase, N-glycosidase, or endoglycoceramidase, and a chemical release method such as hydrazinolysis or β-elimination by alkali treatment. When an O-linked glycan is released from the peptide chain or the like of a glycopeptide or a glycoprotein, the above-described chemical release method such as non-reductive β-elimination is preferably used, and an ammonium carbamate method is more preferably used because degradation caused by peeling is prevented. If necessary, modification may be performed, such as labeling of the reducing end of the glycan with, for example, 3AQ (3-aminoquinoline) or 2AA (2-aminobenzoic acid). Before the treatment for releasing a glycan, cleavage of the peptide chain of a glycopeptide or a glycoprotein, which will be described later, may be performed.

When the sample contains a glycopeptide or a glycoprotein, the glycopeptide or the glycoprotein may be subjected to treatment for causing a reaction to block an amino group, such as dimethylamidation or guanidinylation, if necessary. This makes it possible to prevent a side reaction such as intramolecular dehydration condensation that involves an amino group or a carboxy group present at the end of the main chain. When the peptide chain of the glycopeptide or the glycoprotein to be used has a large number of amino acid residues, the peptide chain is preferably cleaved by, for example, enzymatic cleavage. For example, when a sample for mass spectrometry is prepared, the number of amino acid residues of the peptide chain is preferably 30 or less, more preferably 20 or less, even more preferably 15 or less. On the other hand, when the origin of a peptide to which a glycan is linked needs to be clarified, the number of amino acid residues of the peptide chain is preferably 2 or more, more preferably 3 or more.

Examples of a digestive enzyme used to cleave the peptide chain of the glycopeptide or the glycoprotein include trypsin, Lys-C, arginine endopeptidase, chymotrypsin, pepsin, thermolysin, proteinase K, and proteinase E. These digestive enzymes may be used in combination of two or more of them. Conditions for cleavage of the peptide chain are not particularly limited, and a protocol appropriate to the digestive enzyme to be used is employed. Before the cleavage, denaturation treatment or alkylation treatment may be performed on a protein or a peptide in the sample. Conditions for the denaturation treatment or the alkylation treatment are not particularly limited.

It is to be noted that the cleavage treatment of the peptide chain may be performed before or after any one of reactions to lactonize sialic acid contained in a glycan by the method for preparing an analytical sample according to the present embodiment or after stabilization of lactonized sialic acid. The cleavage of the peptide chain may be achieved not by enzymatic cleavage but by chemical cleavage or the like.

The completion of the step S1001 is followed by a step S1003.

Selective Lactonization Reaction

In the step S1003, the sample is brought into contact with a reaction solution for selective lactonization (hereinafter, referred to as "lactonization reaction solution") to perform a reaction (selective lactonization reaction) so that when sialic acid is linked to the glycan, α2,3-sialic acid is lactonized and α2,6-sialic acid is subjected to modification different from lactonization. In the selective lactonization reaction, α2,8-sialic acid and α2,9-sialic acid can appropriately be lactonized in addition to α2,3-sialic acid.

An operation is performed to remove the lactonization reaction solution from the sample after the selective lactonization reaction. The operation to remove the lactonization reaction solution is not particularly limited as long as an operation to sufficiently lower the concentrations of reagents necessary for the selective lactonization reaction is appropriately performed, and examples of such an operation include: separation of the lactonization reaction solution from the glycan bound to a solid phase carrier by, for example, centrifugation, followed by washing with a washing solution; and evaporation of the sample to dryness by centrifugal concentration.

It is to be noted that timing and the number of times of the removal of the reaction solution are not particularly limited as long as a reaction product selectively lactonized with sufficient reaction specificity can be obtained after a step S1009 that will be described later. The removal of the reaction solution can appropriately be performed after at least one of steps S1003 to S1011.

The lactonization reaction solution contains a dehydration condensation agent and a nucleophilic agent containing an alcohol, an amine, or a salt thereof. The types and concentrations of these dehydration condensation agent and the nucleophilic agent are adjusted so that a dehydration reaction or a nucleophilic reaction selectively occurs on the basis of the linkage type of sialic acid.

A lactone formed by intramolecular dehydration of the carboxy group of α2,3-sialic acid is a six-membered ring, while a lactone that may be formed by intramolecular dehydration of the carboxy group of α2,6-sialic acid is a seven-membered ring. Therefore, α2,3-sialic acid, which generates a six-membered ring more stable than a seven-membered ring, is more easily lactonized than α2,6-sialic acid. Further, the carboxy group of α2,3-sialic acid is present at a position with relatively greater steric hindrance than the carboxy group of α2,6-sialic acid, and therefore α2,3-sialic acid is less likely to react with a large molecule than α2,6-sialic acid. On the basis of such a difference in molecular structure caused by the difference in the linkage type of sialic acid, the types and concentrations of the dehydration condensation agent and the nucleophilic agent are adjusted so that sialic acid is differently modified depending on the linkage type thereof. However, in the method for preparing an analytical sample according to the present embodiment, even when unintended lactonization occurs in the selective lactonization reaction, reaction specificity can be increased by, as will be described later, ring-opening the lactone and again performing the selective lactonization reaction, and therefore it is not necessary to achieve complete reaction specificity by one selective lactonization reaction.

Dehydration Condensation Agent in Selective Lactonization Reaction

The dehydration condensation agent preferably contains a carbodiimide. This is because when a carbodiimide is used, a carboxy group present at a site with great steric hindrance is less likely to be subjected to amidation or the like than when a phosphonium-based dehydration condensation agent (so-called BOP reagent) or an uronium-based dehydration condensation agent is used as the dehydration condensation agent. Examples of the carbodiimide include N,N'-dicyclohexylcarbodiimide (DCC), N-(3-dimethylaminopropyl)-N'-ethylcarbodiimide (EDC), N,N'-diisopropylcarbodiimide (DIC), 1-tert-butyl-3-ethylcarbodiimide (BEC), N,N'-di-tert-butylcarbodiimide, 1,3-di-p-tolylcarbodiimide, bis(2,6-diisopropylphenyl)carbodiimide, bis(trimethylsilyl)carbodiimide, 1,3-bis(2,2-dimethyl-1,3-dioxolan-4-ylmethyl) carbodiimide (BDDC), and salts thereof.

Additive in Selective Lactonization Reaction

In order to promote dehydration condensation caused by the dehydration condensation agent and prevent a side reaction, a highly-nucleophilic additive is preferably used in addition to the carbodiimide. Preferred examples of the highly-nucleophilic additive include 1-hydroxybenzotriazole (HOBt), 1-hydroxy-7-aza-benzotriazole (HOAt), 4-(dimethylamino)pyridine (DMAP), ethyl 2-cyano-2-(hydroxyimino) acetate (Oxyma), N-hydroxy-succinimide (HOSu), 6-chloro-1-hydroxy-benzotriazole (Cl-HoBt), and N-hydroxy-3,4-dihydro-4-oxo-1,2,3-benzotriazine (HOOBt).

Nucleophilic Agent in Selective Lactonization Reaction

The amine used as the nucleophilic agent preferably contains a primary or secondary alkylamine having 2 to more carbon atoms. Preferred examples of the primary alkylamine include ethylamine, propylamine, isopropylamine, butylamine, sec-butylamine, and tert-butylamine. Preferred examples of the secondary alkylamine include dimethylamine, ethylmethylamine, diethylamine, propylmethylamine, and isopropylmethylamine. From the viewpoint of making a carboxy group present at a site with great steric hindrance, such as the carboxy group of α2,3-sialic acid, less likely to be amidated, an amine having a branched alkyl group, such as isopropylamine, is preferably used. When an amine is used as the nucleophilic agent constituting the lactonization reaction solution, the carboxy group of part of sialic acid, such as α2,6-sialic acid, is amidated on the basis of the linkage type of sialic acid.

The alcohol used as the nucleophilic agent is not particularly limited, and may be, for example, methanol or ethanol. When an alcohol is used as the nucleophilic agent constituting the lactonization reaction solution, the carboxy group of part of sialic acid, such as α2,6-sialic acid, is esterified on the basis of the linkage type of sialic acid.

It is to be noted that the nucleophilic agent may contain a salt of the above-mentioned example of the nucleophilic agent.

Concentrations of Dehydration Condensation Agent and Nucleophilic Agent

The concentration of the dehydration condensation agent in the lactonization reaction solution is, for example, preferably 1 mM to 5 M, more preferably 10 mM to 3 M. When a carbodiimide and a highly-nucleophilic additive such as Oxyma, HOAt, or HOBt are used in combination, the concentration of each of them is preferably within the above range. The concentration of the nucleophilic agent in the lactonization reaction solution is preferably 0.01 to 20 M, more preferably 0.1 M to 10 M. The reaction temperature during the selective lactonization reaction is preferably about −20° C. to 100° C., more preferably −10° C. to 50° C.

Phase for Selective Lactonization Reaction

The selective lactonization reaction can be performed in either a liquid phase or a solid phase. When performed in a liquid phase, the reaction is preferably performed in a non-aqueous solvent such as dimethylsulfoxide (DMSO) or dimethylformamide (DMF). When the reaction is performed in a non-aqueous solvent, a side reaction tends to be prevented, which is preferred when a glycopeptide or a glycoprotein is used as a sample. The concentration of each component in the liquid phase reaction is not particularly limited, and can be appropriately determined depending on the type etc. of the dehydration condensation agent or the amine.

When the selective lactonization reaction is performed in a solid phase, a solid phase carrier is not particularly limited as long as the solid phase carrier can immobilize a glycan, a glycopeptide, a glycoprotein, or the like. In order to immobilize, for example, a glycopeptide or a glycoprotein, a solid phase carrier having, as a ligand, an epoxy group, a tosyl group, a carboxy group, an amino group, or the like can be used. In order to immobilize a glycan, a solid phase carrier having, as a ligand, a hydrazide group, an aminooxy group, or the like can be used. It is also preferred that a glycan is adsorbed to a carrier, that is, a stationary phase for hydrophilic interaction chromatography (hereinafter, referred to as "HILIC"), and it is more preferred that this carrier for HILIC contains an amide group. When the reaction is performed in a state where the sample is immobilized on a solid phase carrier, the reaction solution after the reaction can easily be removed, and therefore sialic acid can efficiently be modified.

If necessary, the sample after the selective lactonization reaction may be subjected to treatment such as purification, desalting, solubilization, concentration, or drying by, for example, a known method. The same goes for before and after each reaction shown in the flowchart of FIG. 1.

The completion of the step S1003 is followed by a step S1005.

Ring-Opening Reaction

In the step S1005, a reaction (ring-opening reaction) (hereinafter, the expression "ring-opening reaction" refers to the ring-opening reaction in the step S1005 unless otherwise specified) is performed in which the lactone formed in the selective lactonization reaction is ring-opened by bringing the sample into contact with a solvent (hereinafter, referred to as "solvent for ring-opening reaction"). As described above, when the selective lactonization reaction is performed, there is a case where α2,6-sialic acid is lactonized in at least an O-linked glycan. A lactone formed by unintentional lactonization of α2,6-sialic acid is opened by this ring-opening reaction. On the other hand, sialic acid modified by modification different from lactonization, such as amidation, in the selective lactonization reaction is kept modified without change. The expression "unintentionally lactonized" means that sialic acid that should be modified by modification different from lactonization is lactonized because reaction specificity achieved by one selective lactonization reaction is not sufficient.

Solvent for Ring-Opening Reaction

The solvent for ring-opening reaction is not particularly limited, and any solvent can be used. Although it may take several tens of hours, the ring-opening reaction of the lactone can be caused by hydrolysis even when water is used as the solvent for ring-opening reaction. In order to efficiently prepare an analytical sample, the lactone is preferably ring-opened by the solvent for ring-opening reaction in a shorter period of time. From such a viewpoint, the solvent for ring-opening reaction is preferably a basic solvent, more preferably a basic solvent having a pH of 8 or higher, even more preferably a basic solvent having a pH of 10 or higher. A basic solvent is more suitable than an acidic solvent for lactone hydrolysis. However, from the viewpoint of rapidly performing the ring-opening reaction, the solvent for ring-opening reaction is also preferably an acidic solvent, more preferably an acidic solvent having a pH of 6 or lower, even more preferably an acidic solvent having a pH of 4 or lower.

From the viewpoint of preventing the solvent for ring-opening reaction from unintentionally reacting with sialic acid, it is preferred that the solvent for ring-opening reaction does not contain an alcohol, an amine, or a salt thereof. However, the solvent for ring-opening reaction may contain an alcohol, an amine, or a salt thereof as long as a reaction product selectively lactonized with sufficient reaction specificity can be obtained after a step S1009 that will be described later. When the solvent for ring-opening reaction contains an amine, the amine is preferably one that is not in the form of a salt. The solvent for ring-opening reaction is preferably, for example, an aqueous sodium hydroxide solution because it is readily available and strongly basic. The aqueous sodium hydroxide solution more preferably has a concentration of 5 wt % or less from the viewpoint of the risk of handling it of the like. Another preferred example of the solvent for ring-opening reaction is one containing a quaternary alkyl ammonium cation or tetramethylguanidine as a strong base.

Time Needed for Ring-Opening Reaction

The time during which the sample subjected to the selective lactonization reaction is in contact with the solvent for ring-opening reaction is not particularly limited. Depending on the type of the solvent for ring-opening reaction, the time is preferably 10 minutes or shorter. From the viewpoint of efficiently preparing an analytical sample, the time is preferably a short time of several seconds or shorter. As will be described later, when the sample is immobilized on a solid phase, the ring-opening reaction may be caused by allowing the solvent for ring-opening reaction to pass through the solid phase for, for example, several seconds.

Phase for Ring-Opening Reaction

The ring-opening reaction can be performed in either a liquid phase or a solid phase. When the selective lactonization reaction is performed in a state where the sample is immobilized on a solid phase, the sample subjected to the selective lactonization reaction may be kept immobilized on the solid phase when the ring-opening reaction is performed. Alternatively, the sample may be immobilized onto a solid phase after subjected to the selective lactonization reaction to perform the ring-opening reaction.

When the ring-opening reaction is performed in a solid phase, the same solid phase carrier as that described above with reference to the selective lactonization reaction can be used. The sample can be immobilized onto the solid phase carrier under the conditions described above with reference to the selective lactonization reaction. The sample can be released from the solid phase carrier under conditions that will be described later with reference to a stabilization reaction. When the reaction is performed in a state where the sample is immobilized on the solid phase carrier, for example, the solvent for ring-opening reaction after the ring-opening reaction can easily be removed, and therefore sialic acid can efficiently be modified.

The completion of the step S1005 is followed by a step S1007.

In the step S1007, the selective lactonization reaction is again performed. At least part of sialic acids unintentionally lactonized in the selective lactonization reaction performed in the step S1003 is subjected to modification different from lactonization by the selective lactonization reaction in the step S1007. Sialic acid of a specific linkage type, such as α2,3-sialic acid, intended to be lactonized by the selective lactonization reaction is lactonized every time the selective lactonization reaction is performed, and is ring-opened every time the ring-opening reaction is performed.

The completion of the step S1007 is followed by a step S1009.

In the step S1009, the step S1005 and the step S1007 are further alternately performed repeatedly a predetermined number of times. By the ring-opening reaction and the selective lactonization reaction performed subsequently to the ring-opening reaction, the lactone formed by unintentional lactonization of sialic acid is ring-opened and modification is again performed on the basis of reaction specificity achieved by one selective lactonization reaction. Sialic acid modified by modification other than lactonization remains as it is even when the reactions are subsequently performed so that the number of sialic acids to be unintentionally lactonized decreases as the reactions are repeatedly performed. Therefore, the linkage-specific selective lactonization reaction can accurately be performed by repeating a combination of the ring-opening reaction and the selective lactonization reaction.

The number of repetitions of the selective lactonization reaction in the step S1009 (hereinafter, referred to as "number of repetitions") is not particularly limited. When the number of repetitions is larger, total reaction specificity achieved by two or more selective lactonization reactions is higher, and therefore the number of repetitions is preferably one or more, more preferably two or more. If the number of repetitions is too large, the efficiency of preparing an analytical sample is reduced, and therefore the number of repetitions can appropriately be set to, for example, 100 or less or 10 or less.

The completion of the step S1009 is followed by a step S1011.

It is to be noted that when a sample selectively lactonized with desired reaction specificity can be obtained in the step S1007, the step S1009 may be omitted.

Stabilization Reaction

In the step S1011, a reaction to stabilize lactonized sialic acid (hereinafter, referred to as "stabilization reaction") is performed by bringing the sample into contact with a reaction solution for performing modification to stabilize sialic acid where lactone is formed (hereinafter, referred to as "stabilization reaction solution"). In the stabilization reaction, α2,3-sialic acid or the like lactonized by the selective lactonization reaction is subjected to modification different from that is performed on α2,6-sialic acid in the step S1003 to obtain an analytical sample.

It is to be noted that the step S1011 may be omitted, in which case the selectively-lactonized sample is analyzed by, for example, mass spectrometry, chromatography, or a combination of them.

In the stabilization reaction, the type of reaction for modifying the sialic acid-derived lactone formed by the selective lactonization reaction is not particularly limited, and may be amidation, esterification, or the like. The amidation or esterification is preferably performed on a carboxy group having a carbon atom contained in the lactone. When the modification is performed by amidation, the stabilization reaction solution contains ammonia, an amine, or a salt thereof. When the modification is performed by esterification, the stabilization reaction solution contains an alcohol.

When the analytical sample obtained after the stabilization reaction is analyzed by mass spectrometry, the lactone is modified in the step S1011 so that modified products are formed which are different in mass depending on the linkage type of sialic acid. In other words, for example, in the step S1003, a lactone is formed on sialic acid of a first linkage type, and a modified product A that is derived from sialic acid of a second linkage type different from the first linkage type and that is different from the lactone is formed. In such a case, a modified product B that is derived from the sialic acid of the first linkage type and that is different in mass from the modified product A is formed in the step S1011. Here, the difference in mass between the modified product A and the modified product B is set to be large to the extent that they can be sufficiently differentiated on the basis of mass resolution in the analysis of the analytical sample by mass spectrometry. The above-described sialic acid of the first linkage type preferably includes at least one of α2,3-sialic acid, α2,8-sialic acid, and α2,9-sialic acid, and the above-described sialic acid of the second linkage type preferably includes α2,6-sialic acid.

When the analytical sample obtained after the stabilization reaction is analyzed by chromatography, modified products are formed in the step S1011 so as to be different in substituent group depending on the linkage type of sialic acid, which is preferred in that separation by chromatography is promoted.

An example of the stabilization reaction is lactone ring-opening and subsequent amidation described in PTL 2. In this case, for example, the lactone is ring-opened through contact between the sample and a basic solvent, an acidic solvent, or the like. Then, ring-opened sialic acid can be amidated by bringing the sample into contact with the stabilization reaction solution containing an amine such as a primary alkylamine (e.g., methylamine or ethylamine) or a salt thereof and a dehydration condensation agent. Here, the dehydration condensation agent may contain a phosphonium-based dehydration condensation agent such as phosphonium hexafluorophosphate (PyBOP) or an uronium-based dehydration condensation agent. Further, from the viewpoint of increasing amidation efficiency, N-methylmorpholine (NMM) may be added to the stabilization reaction solution.

Alternatively, the stabilization reaction may be performed by bringing the sample into contact with a stabilization reaction solution to convert sialic acid from a lactonized form to an amidated form at a time. In this case, the sample is brought into contact with the stabilization reaction solution containing an amine such as a primary alkylamine (e.g., methylamine or ethylamine) or a salt thereof. The above-described conversion is allowed to easily occur by creating a basic condition with a pH of, for example, 8 or higher, preferably 10 or higher. In this case, no dehydration condensation agent is necessary, but the stabilization reaction solution may contain a dehydration condensation agent.

Phase for Stabilization Reaction

The stabilization reaction can be performed in either a liquid phase or a solid phase. The state of the sample to be subjected to the stabilization reaction is not particularly limited as long as the sample can be brought into contact with the stabilization reaction solution. However, it is preferred that the sample is brought into contact with the stabilization reaction solution in a state where the glycan contained in the sample is bound or adsorbed to a solid phase carrier.

When the reaction is performed in a solid phase, the same solid phase carrier as that described above with reference to the selective lactonization reaction can be used. The sample can be immobilized onto the solid phase carrier under the conditions described above with reference to the selective lactonization reaction.

After the sample immobilized on the solid phase carrier is subjected to the action of the stabilization reaction solution to modify the lactone, the sample is released from the carrier by, for example, a chemical method or an enzymatic reaction and collected. For example, a glycoprotein or a glycopeptide immobilized on a carrier may be collected by enzymatic cleavage using a glycosidase such as PNGase F or a digestive enzyme such as trypsin or by chemical cleavage, or a glycan bound to a solid phase carrier having a hydrazide group may be collected by releasing it using a weak acidic solution. In HILIC, the sample can be eluted using an aqueous solution such as water after performing a stabilization reaction using a stabilization reaction solution containing a solvent such as acetonitrile.

When the sample is reacted in a state where it is immobilized on a solid phase carrier, removal of the reaction solution and desalting and purification can more easily be performed, which simplifies sample preparation. Further, when a solid phase carrier is used, and the sample is immobilized onto the solid phase carrier in the form of a glycoprotein or a glycopeptide, subjected to the stabilization reaction, and cleaved with a glycosidase such as PNGase F, the sample after the stabilization reaction can be collected as a free glycan.

The completion of the step S1011 is followed by a step S1013.

In the step S1013, the sample is analyzed by mass spectrometry, chromatography, or a combination of them. The above-described selective lactonization reaction results in a difference in mass between a glycan containing sialic acid that is less likely to be lactonized, such as $\alpha 2,6$ sialic acid, and a glycan containing sialic acid that is likely to be lactonized, such as $\alpha 2,3$-sialic acid, $\alpha 2,8$-sialic acid, or $\alpha 2,9$-sialic acid. Therefore, these glycans can be separated by mass spectrometry on the basis of the linkage type of sialic acid.

An ionization method used in the mass spectrometry is not particularly limited, and may be, for example, matrix-assisted laser desorption/ionization (MALDI), electrospray ionization (ESI), or nanoelectrospray ionization (nano-ESI). The ionization method is particularly preferably MALDI. The ionization mode in the mass spectrometry may be either positive or negative. The mass spectrometry may be performed in multiple stages, in which case the structure of a glycan or the structure of a peptide chain can appropriately be analyzed in addition to the linkage type of sialic acid.

Alternatively, the sample may be analyzed by an analysis method other than mass spectrometry, such as chromatography, on the basis of the properties of modified products formed as a result of the selective lactonization reaction and the stabilization reaction. A column used in liquid chromatography is not particularly limited, and a hydrophobic reverse phase column such as C30, C18, C8, or C4, a carbon column, or a normal-phase column for HILIC may appropriately be used. It is preferred that after liquid chromatography is performed, measurement is performed by mass spectrometry to precisely analyze components in the sample through multiple separation. In this case, it is more preferred that an eluate from a liquid chromatograph is directly ionized by, for example, ESI in a mass spectrometer under online control.

When the step S1013 is completed, the procedure is terminated.

Kit for Preparing Analytical Sample

A kit for preparing an analytical sample (hereinafter, referred to as "preparation kit") is provided which is suitable for use in the method for preparing an analytical sample according to the present embodiment. The content of the preparation kit is not particularly limited as long as the preparation kit includes the above-described solvent for ring-opening reaction such as a basic solvent having a pH of 8 or higher, and the preparation kit may include a reagent or any consumable supply other than a reagent for use in mass spectrometry. The use of the preparation kit makes it possible to prepare an analytical sample more efficiently.

According to the above-described embodiment, it is possible to obtain the following functions and effects.

(1) The method for preparing an analytical sample according to the present embodiment includes: performing a selective lactonization reaction so that when sialic acid is linked to a glycan, sialic acid of a first linkage type (e.g., $\alpha 2,3$-) is lactonized and modification different from lactonization is performed on sialic acid of a second linkage type (e.g., $\alpha 2,6$-) different from the first linkage type; performing a ring-opening reaction to ring-open a lactone formed in the selective lactonization reaction; and performing the selective lactonization reaction again. This makes it possible to more accurately modify sialic acid in a linkage-specific manner.

(2) In the method for preparing an analytical sample according to the present embodiment, the lactone formed by lactonization of the sialic acid of the second linkage type is ring-opened in the ring-opening reaction. This makes it possible to prevent the sialic acid of the second linkage type in a lactone form from being subjected to a stabilization reaction or an analysis such as mass spectrometry.

(3) The method for preparing an analytical sample according to the present embodiment further includes repeatedly performing an operation to perform the ring-opening reaction and an operation to perform the selective lactonization reaction alternately a predetermined number of times equal to or more than 1. This makes it possible to decrease the ratio of sialic acid to be unintentionally lactonized to more accurately modify sialic acid in a linkage-specific manner.

(4) In the method for preparing an analytical sample according to the present embodiment, the ring-opening reaction is performed by bringing the sample subjected to the selective lactonization reaction into contact with a basic solvent or the like having a pH of 8 or higher. This makes it possible to efficiently prepare an analytical sample under a basic condition where the lactone is easily ring-opened.

(5) In the method for preparing an analytical sample according to the present embodiment, at least one of reactions including the selective lactonization reaction and the ring-opening reaction may be performed in a state where the glycan is bound or adsorbed to a solid phase carrier. This facilitates removal of a reaction solution or desalting and purification to efficiently prepare an analytical sample.

(6) In the method for preparing an analytical sample according to the present embodiment, the modification performed on the sialic acid of the second linkage type is esterification or amidation. This makes it possible to prepare an analytical sample in which the sialic acid of the second linkage type is stabilized.

(7) In the method for preparing an analytical sample according to the present embodiment, the lactone formed by the selective lactonization reaction is subjected to modification different from that is performed on the sialic acid of the second linkage type. This makes it possible to prepare an analytical sample in which the sialic acid of the first linkage type is stabilized.

(8) An analysis method according to the present embodiment includes: preparing an analytical sample by the method for preparing an analytical sample according to the present embodiment; and analyzing the prepared analytical sample. This makes it possible to differentiate sialic acids of different linkage types with high accuracy in the analysis of the glycan.

(9) In the analysis method according to the present embodiment, the prepared analytical sample may be analyzed by at least one of mass spectrometry and chromatography. This makes it possible to differentiate sialic acids of different linkage types in the analysis of the glycan on the basis of a linkage-specific mass difference or influence on separation in chromatography.

(10) A kit for preparing an analytical sample according to the present embodiment includes a basic solvent having a pH of 8 or higher. This makes it possible to rapidly supply or provide a solvent for ring-opening reaction.

The present invention is not limited to the contents of the above-described embodiment. Other embodiments within the scope of the technical idea of the present invention are also included in the scope of the present invention.

EXAMPLES

Hereinbelow, examples of the present embodiment will be described. However, the present invention is not limited to the following examples. Hereinafter, "%" denotes "% by weight" unless otherwise specified.

A sample containing, as glycans having known structures, O-linked glycans released from bovine Fetuin by non-reductive β elimination was analyzed to determine the degree of accuracy of linkage-specific modification of sialic acid.

Non-Reductive β Elimination Treatment

Twenty microliters of a 10 μg/μL Fetuin solution was mixed with 30 mg of ammonium carbamate, and the mixture was well stirred with a vortex mixer to dissolve at least part of the ammonium carbamate. The solution in which Fetuin was dissolved was incubated in an incubator at 60° C. for 20 hours to perform non-reductive β elimination. Then, 500 μL of $H_2O$ was added to the sample, and the mixture was subjected to vacuum centrifugal concentration at 70° C., which was repeated three times to remove the excess ammonium carbamate.

Immobilization of O-linked Glycan onto Hydrazide Beads

The sample subjected to non-reductive β elimination was bound to a solid phase carrier (included in a glycan purification kit "BlotGlyco" (Sumitomo Bakelite Co., Ltd.)) comprising beads having a hydrazide group as a ligand. The binding of the glycans to the solid phase carrier was performed in accordance with a standard protocol of the glycan purification kit "BlotGlyco".

Linkage-Specific Modification on Hydrazide Beads

The sample immobilized on the hydrazide beads was subjected to linkage-specific modification of sialic acid by a conventional method or a method according to the above-described embodiment (improved method).

Conventional Method

The carrier to which the glycans had been bound was washed three times with 200 μL of DMSO. Then, 100 μL of a selective lactonization reaction solution containing isopropylamine (2 M isopropylamine hydrochloride, 500 mM EDC-HCl, 500 mM Oxyma) was added to the carrier, and the mixture was reacted for 1.5 hours while being gently stirred at 800 rpm (as a result, α2,6-sialic acid and α2,3-sialic acid are converted to isopropylamide and a lactone form, respectively). The selective lactonization reaction solution was removed by centrifugation, and then the carrier was washed once with 200 μL of methanol. Then, the carrier was washed three times with 200 μL of a 1% aqueous methylamine solution to cleave the lactone. Then, the carrier was washed twice with 200 μL of methanol and three times with 200 μL of DMSO. Then, 100 μL of a stabilization reaction solution (1 M methylamine hydrochloride, 250 mM PyBOP, 15% NMM) was added to the carrier, and the mixture was stirred at room temperature for 1 hour to perform methylamidation of the lactone form. Then, the carrier was washed three times with 200 μL of DMSO, three times with 200 μL of methanol, and three times with 200 μL of water.

Improved Method

The carrier to which the glycans had been bound was washed three times with 200 μL of DMSO. Then, 100 μL of a selective lactonization reaction solution containing isopropylamine (2 M isopropylamine hydrochloride, 500 mM EDC-HCl, 500 mM Oxyma) was added to the carrier, and the mixture was reacted for 0.5 hours while being gently stirred at 800 rpm. The selective lactonization reaction solution was removed by centrifugation, and then the carrier was washed once with 200 μL of methanol. Then, the carrier was washed three times with 200 μL of a 1% aqueous isopropylamine solution used as a solvent for ring-opening reaction to cleave the lactone. Then, the carrier was washed twice with 200 μL of methanol and three times with 200 μL of DMSO. Then, 100 μL of a selective lactonization reaction solution containing isopropylamine was again added to the carrier, and the mixture was reacted for 0.5 hours while being gently stirred at 800 rpm. Then, the carrier was washed with a 1% aqueous isopropylamine solution in the same manner as described above to cleavage the lactone. Then, 100 μL of a selective lactonization reaction solution containing isopropylamine was further added to the carrier, and the mixture was reacted for 0.5 hours while being gently stirred at 800 rpm. Then, the carrier was washed three times with 200 μL of a 1% aqueous methylamine solution to cleave the lactone. Then, the carrier was washed twice with 200 μL of methanol and three times with 200 μL of DMSO. Then, 100 μL of a stabilization reaction solution (1 M methylamine hydrochloride, 250 mM PyBOP, 15% NMM) was added to the carrier, and the mixture was stirred at room temperature for 1 hour. Then, the carrier was washed three times with 200 μL of DMSO, three times with 200 μL of methanol, and three times with 200 μL of water.

Release of Glycans from Hydrazide Beads, Labeling of Glycans, Mass Spectrometry

The glycan sample after stabilization reaction was released from the carrier in accordance with a standard protocol of BlotGlyco. More specifically, 20 μL of $H_2O$ and 180 μL of 2% acetic acid/acetonitrile were added to the carrier, and the mixture was heated at 70° C. for 1.5 hours without a lid to evaporate the solvent and release the glycans. Then, the glycans were collected by performing elution three times using 50 μL of $H_2O$. The collected glycans were subjected to desalting and purification using Stage Tip Carbon and evaporated to dryness by vacuum centrifugal concentration. Stage Tip Carbon is a carbon tip prepared by packing Empore Disk-Carbon (manufactured by 3M) cut to have a diameter of about 1 mm in a 200-μL tip. In the desalting and purification, 100 μL of acetonitrile (ACN) was added to Stage Tip Carbon and discharged by centrifugation. Then, the same operation was performed using 1 M NaOH, 1 M HCl, $H_2O$, a 80% ACN/0.1% trifluoroacetic acid (TFA) solution, and $H_2O$ in order, to wash and equilibrate the column carrier. Then, the solution containing the released glycans was added to the column and discharged by centrifugation. Further, 150 μL of $H_2O$ was added and then discharged by centrifugation, which was repeated three times to perform washing. Finally, 20 μL of a 80% ACN/0.1% TFA solution was added and discharged by centrifugation, which was repeated twice to elute the glycans. The two eluates were mixed and evaporated to dryness by removing the solvent using SpeedVac (Themo Fisher Scientific K.K.)

The dried sample was re-dissolved in 10 μL of $H_2O$, and 1 μL of the resulting solution was dropped onto a focus plate, and 0.5 μL of a solution obtained by dissolving 100 mM 3AQ/CA (3-aminoquinoline/p-coumaric acid) as a matrix and 2 mM ammonium dihydrogen phosphate in 50% ACN was added. Then, the focus plate was placed on a heat block at 75° C. to perform a reaction for 1.5 hours to label the reducing ends of the glycans with 3AQ. After the completion of the reaction, the plate was cooled to room temperature, and time-of-flight mass spectrometry was performed in negative ion mode using a MALDI-QIT-TOF-MS (AXIMA-Resonance, Shimadzu/Kratos).

Figure 2:
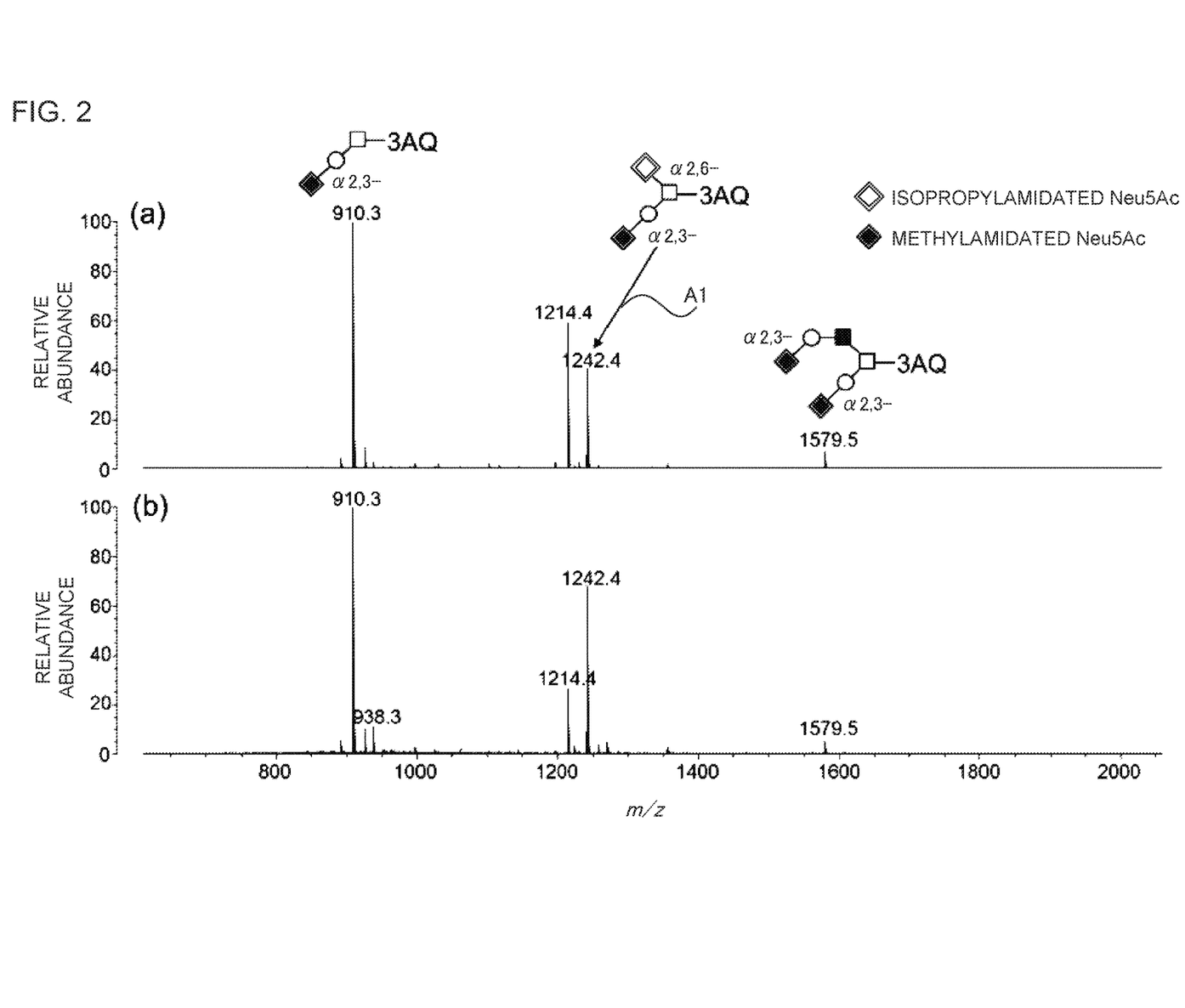
FIG. 2 shows a mass spectrum (top) of an analytical sample obtained by a conventional method for preparing an analytical sample and a mass spectrum (bottom) of an analytical sample obtained by a method for preparing an analytical sample according to the embodiment.

FIG. 2 shows negative ion mass spectra (a) and (b) of the above-described mass spectrometry obtained by the conventional method and the improved method, respectively. The structures of the O-linked glycans of Fetuin are known, and are therefore shown so as to correspond to their respective peaks. When α2,3-sialic acid and α2,6-sialic acid in the glycan are methylamidated and isopropylamidated, respectively, a peak is observed at about m/z 1242.13 (see an arrow A1). In the mass spectrum (a) obtained by the conventional method, a peak corresponding to m/z 1214.4 whose difference from the above m/z value corresponds to −28 Da is observed with a higher intensity than the above peak. The peak at m/z 1214.4 corresponds to a reaction product accidentally obtained by unintentional lactonization of α2,6-sialic acid (the peak appears due to methylamidation (MA) of α2,6-sialic acid that was intended to be subjected to isopropylamidation (iPA)). In the mass spectrum (b) obtained by the improved method, the intensity of the peak derived from the accidentally-obtained reaction product was significantly reduced, and the peak corresponding to a reaction product properly obtained by iPA of α2,6-sialic acid is observed with higher intensity.

In spite of the fact that the reaction time of the selective lactonization reaction in the conventional method and the total reaction time of the selective lactonization reaction in the improved method are equally 1.5 hours, the ratio of the accidentally-obtained reaction product was reduced in the case of the improved method. This is because the operation for lactone cleavage is performed between the selective lactonization reactions in the improved method.

The invention claimed is:

1. A method for preparing an analytical sample for analyzing a glycan contained in a sample, comprising:
    performing a first reaction so that when sialic acid is linked to the glycan, sialic acid of a first linkage type is lactonized and modification different from lactonization is performed on sialic acid of a second linkage type different from the first linkage type;
    performing a second reaction to ring-open a lactone formed in the first reaction; and
    after performing the second reaction, performing the first reaction again.

2. The method for preparing an analytical sample according to claim 1, wherein
    the lactone formed by lactonization of the sialic acid of the second linkage type is ring-opened in the second reaction.

3. The method for preparing an analytical sample according to claim 1, further comprising:
    repeatedly performing an operation to perform the second reaction and an operation to perform the first reaction alternately a predetermined number of times equal to or more than 1.

4. The method for preparing an analytical sample according to claim 2, further comprising:
    repeatedly performing an operation to perform the second reaction and an operation to perform the first reaction alternately a predetermined number of times equal to or more than 1.

5. The method for preparing an analytical sample according to claim 1, wherein
    the second reaction is performed by bringing the sample subjected to the first reaction into contact with a basic solvent having a pH of 8 or higher.

6. The method for preparing an analytical sample according to claim 2, wherein
    the second reaction is performed by bringing the sample subjected to the first reaction into contact with a basic solvent having a pH of 8 or higher.

7. The method for preparing an analytical sample according to claim 3, wherein
    the second reaction is performed by bringing the sample subjected to the first reaction into contact with a basic solvent having a pH of 8 or higher.

8. The method for preparing an analytical sample according to claim 4, wherein
    the second reaction is performed by bringing the sample subjected to the first reaction into contact with a basic solvent having a pH of 8 or higher.

9. The method for preparing an analytical sample according to claim 1, wherein
    at least one of reactions including the first reaction and the second reaction is performed in a state where the glycan is bound or adsorbed to a solid phase carrier.

10. The method for preparing an analytical sample according to claim 1, wherein
    the sample contains an O-linked glycan.

11. The method for preparing an analytical sample according to claim 1, wherein
    the modification is esterification or amidation.

12. The method for preparing an analytical sample according to claim 1, wherein
    the lactone formed by the first reaction is subjected to modification different from the modification performed on sialic acid of the second linkage type.

13. The method for preparing an analytical sample according to claim 1, wherein
    the sialic acid of the first linkage type is at least one of α2,3-sialic acid, α2,8-sialic acid, and α2,9-sialic acid, and the sialic acid of the second linkage type is α2,6-sialic acid.

14. An analysis method comprising:
    preparing an analytical sample by the method for preparing an analytical sample according to claim 1; and
    analyzing the prepared analytical sample.

15. The analysis method according to claim 10, wherein
    the prepared analytical sample is analyzed by at least one of mass spectrometry and chromatography.

* * * * *